United States Patent [19]

Kiener et al.

[11] Patent Number: 5,284,767
[45] Date of Patent: Feb. 8, 1994

[54] MICROORGANISMS USEFUL FOR THE PRODUCTION OF HYDROXYLATED HETEROCYCLES

[75] Inventors: Andreas Kiener, Visp, Switzerland; Yvonne van Gameren, Ridderkerk, Netherlands; Michael Bokel, Visp, Switzerland

[73] Assignee: Lonza Ltd., Gampel-Valais, Switzerland

[21] Appl. No.: 919,275

[22] Filed: Jul. 27, 1992

Related U.S. Application Data

[62] Division of Ser. No. 764,763, Sep. 24, 1991, Pat. No. 5,229,278.

[30] Foreign Application Priority Data

Sep. 25, 1990 [CH] Switzerland ............... 3091/90

[51] Int. Cl.$^5$ ............... C12R 1/01; C12R 1/06; C12P 17/12; C12N 1/20
[52] U.S. Cl. ............... 435/252.1; 435/122; 435/822; 435/830
[58] Field of Search ............... 435/252.1, 830, 822, 435/122

[56] References Cited

U.S. PATENT DOCUMENTS 4,814,444 3/1989 Malz, Jr. et al. ............... 544/354

OTHER PUBLICATIONS

"ATCC Catalogue of Bacteria & Bacteriophages" 17th Ed 1989 pp. 20–21 and 185.
Maga and Sizer, J. Agr. Food Chem., 21, (1973), pp. 22 to 30.
Karmas and Spoerri, J. Amer. Chem., 74, (1952), pp. 1580 to 1584.
Matley and Harle, Biochem. Soc., Trans., 4, (1976), pp. 492 to 493.
Soini and Pakarinen, FEMS Microbiol Lett., (1985), pp. 167 to 171.
Drews, G., Microbiologisches Praktikum, 4th Ed., Springer Verlag, (1983), pp. 1 to 8.

Primary Examiner—Herbert J. Lilling
Attorney, Agent, or Firm—Fisher, Christen & Sabol

[57] ABSTRACT

Microorganisms which are capable of growing with 2,5-dimethylpyrazine as the sole carbon, nitrogen and energy source. These microorganisms hydroxylate heterocycles of general formula:

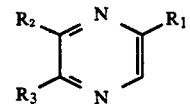

I or

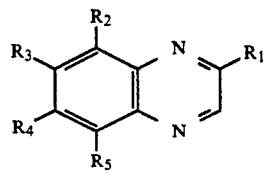

II to heterocycles of general formula:

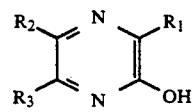

III or

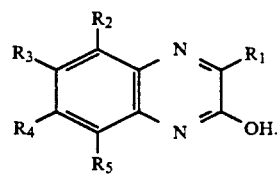

IV

The latter compounds are accumulated in the growth medium.

7 Claims, No Drawings

MICROORGANISMS USEFUL FOR THE PRODUCTION OF HYDROXYLATED HETEROCYCLES

This is a divisional application of Ser. No. 07/764,763, filed Sep. 24, 1991, now U.S. Pat. No. 5,229,278.

BACKGROUND OF THE INVENTION

1. Field Of The Invention

The invention relates to microorganisms, which grow with 2,5-dimethylpyrazine, and hydroxylate pyrazines or quinoxalines of general formula:

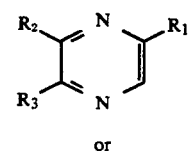

I or

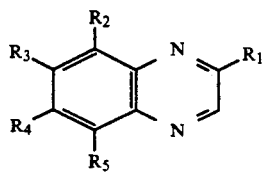

II as well as to a process for the production of hydroxylated pyrazines or quinoxalines.

2. Background Art

Hydroxylated pyrazines are, for example, important intermediate products for the production of methoxylalkylpyrazines. Methoxyalkylpyrazines are essential components of aromatic substances [Maga and Sizer, J. Agric. Food Chem., 21, (1973), pp. 22 to 30]. Hydroxylated quinoxalines are, for example, important pharmaceutical intermediate products (U.S. Pat. No. 4,814,444).

Thus far, only chemical processes for the production of hydroxylated quinoxalines and hydroxylated pyrazines are known. For example, U.S. Pat. No. 4,814,444 describes a process in which 6-chloro-2-hydroxyquinoxaline-4-oxide is reduced in the presence of a catalyst to 6-chloro-2-hydroxyquinoxaline. But this process has the drawback that it is currently not feasible on an industrial scale.

A chemical process for the production of hydroxylated pyrazines is described, for example, in Karmas and Spoerri, J. Amer. Chem., 74, (1952), pp. 1580 to 1584, in which, for example, 2-hydroxy-5-methylpyrazine is synthesized starting from methylglyoxal and glycinamide hydrochloride. But this process has the drawback that the product is highly contaminated.

Also, studies on the biological catabolism of 2-hydroxypyrazine in Matley and Harle, Biochem. Soc. Trans., 4, (1976), pp. 492 to 493, and studies on 2-pyrazinecarboxamide in Soini and Pakarinen. FEMS Microbiol. Lett., (1985), pp. 167 to 171, are described. But no microorganisms have become known which hydroxylate pyrazines or quinoxalines of general formula I or II (set out herein) and accumulate the latter in a growth medium.

BROAD DESCRIPTION OF THE INVENTION

The main object of the invention is to find and provide a new type of microorganism, which is capable in a simple way of hydroxylating regiospecifically-substituted pyrazines or quinoxalines of general formula I or II, as well as providing a process for the production of hydroxylated pyrazines and quinoxalines. Other objects and advantages of the invention are set out herein or are obvious herefrom to one skilled in the art. The objects and advantages of the invention are achieved by the microorganisms and process of the invention.

The microorganisms of the invention are capable of growing with 2,5-dimethylpyrazine as a sole carbon, nitrogen and energy source, and of converting pyrazines of general formula I as substrate:

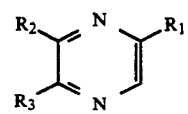

I or quinoxalines or general formula II as substrate:

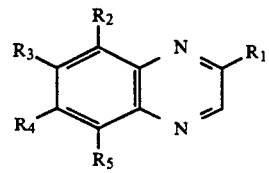

II wherein $R_1$ is a $C_1$-$C_4$ alkyl group or a halogen atom and $R_2$, $R_3$, $R_4$ and $R_5$ are the same or different and each is a hydrogen atom, a $C_1$-$C_4$ alkyl group or a halogen atom, to a hydroxylated pyrazine of general formula III:

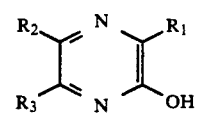

III or to a hydroxylated quinoxaline of general formula IV:

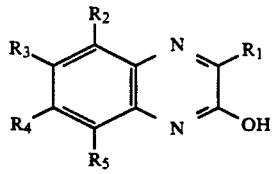

IV wherein $R_1$, $R_2$, $R_3$, $R_4$ and $R_5$ have the above-stated meaning, respectively and the latter is accumulated in the growth medium.

The invention also includes biologically pure and substantially biologically pure cultures of the microorganisms of the invention.

The invention also includes a process of for producing hydroxylated pyrazines and quinoxalines using the microorganisms of the invention.

DETAILED DESCRIPTION OF THE INVENTION

As studies with soil samples from sewage treatment plants, earth, anthills and compost piles have shown, microorganisms, which catabolize 2,5-dimethylpyrazine, are capable of hydroxylating the pyrazines or quinoxalines of general formula I or II. According to the invention, all of these strains that use 2,5-dimethylpyrazine as the sole carbon, nitrogen and energy source are suitable for this hydroxylation, and are selected according to the usual microbiological techniques. Suitably, all gram-positive and gram-negative microorganisms can be used which catabolize 2,5-dimethylpyrazine and hydroxylate the heterocycles of general formula I or II as a substrate to heterocycles of general formula III or IV and are accumulated in the growth medium. The preferred microorganisms are *Rhodococcus erythropolis* having deposit number DSM (German Collection of Microorganisms) No. 6138 and *Arthrobacter sp.* having deposit number DSM No. 6137.

Since the new identification of the microorganisms with DSM No. 6138 and DSM No. 6137 did not take place until after the priority date (that is, based on Swiss Patent Application No. 3091/90, filed on Sep. 25, 1990) of this application, below the microorganism with the earlier designation *Rhodococcus equi* Heida (DSM No. 6138) is now designated as *Rhodococcus erythropolis* (DSM No. 6138) and the microorganism with the earlier designation *Micrococcus sp.* YVG (DSM No. 6137) is now designated as *Arthrobacter sp.* (DSM No. 6137). These strains were deposited on Sep. 7, 1990 in the German Collection of Microorganisms (DSM) and Zellkulturen (Cell Cultures) GmbH, Mascherodeweg 1b, 3300 Braunschweig/FRG.

A scientific description of *Arthrobacter sp.* (DSM No. 6137) is as follows:

Characterization: In young cultures plemorphous rods, in older cultures coccoid to cocci; gram-positive; strictly aerobic, no acid formation from glucose

| mobility | − |
| spores | − |
| catalase | + | mesodiaminopimelic acid in the cell wall: no
Peptidoglycan type: A3alpha, Lys-Ala$_{2-3}$; the alpha-carboxyl group of the D-glutamic acid of the peptide subunit is substituted by a glycine radical.

A scientific description of *Rhodococcus erythropolis* (DSM No. 6138) is as follows:

| Amino acid of the peptidoglycan diaminopimelic acid (DAP) | + |
| Sugar from whole-cell hydrolyzates: | |
| arabinose (ARA) | + |
| galactose (GAL) | + |
| madurose (MAD) | − |
| xylose (XYL) | − |
| glucose (GLU) | + |
| ribose (RIB) | + |

Fatty acids:
Unbranched saturated and unsaturated fatty acids plus tuberculostearic acid present
15 to 30 percent
Mycolic acids:
Micolic acids with a chain length of $C_{35}$–$C_{40}$ percent
Menaquinones:
Type MK-8 (H$_2$) 93 percent
Physiological tests for species-identification of microorganisms containing mycolic acid:

| N-actylglucusamine (NAG) | + |

-continued

| D-glycosaminic acid (GAT) | − |
| D-turanose (TUR) | − |
| 2-hydroxyvalerate (o2V) | + |
| L-alanine (ALA) | + |
| L-proline (PRO) | − |
| tyramine (TYR) | − |
| 4-aminobutyrate (o4B) | + |
| 2-desoxythymidine-s-pup-phosphate (CDP) | + |
| galactose (GAL) | − |
| L-rhamnose (RHA) | − |
| aralite (ARA) | + |
| 2-oxo-glutarate (o2G) | − |
| 4-aminobutyrate (a4B) | − |
| L-serine (SER) | + |
| acetamide (ATA) | + |
| quinate (QUI) | + |
| D-glucarate (GCT) | − |
| D-ribose (RiB) | + |
| inositol (INO) | + |
| pimelase (PIM) | + |
| L-aspartate (ASP) | − |
| L-valine (VAL) | + |
| benzoate (BEN) | − |
| pNP-beta-D-xyloside (CXY) | + |
| gluconate (GDT) | + |
| sucrose (D-saccharose; SUC) | + |
| citrate (CIT) | + |
| succinate (SAT) | + |
| L-leucine (LEU) | + |
| putrescine (PUT) | + |
| 3-hydroxybenzoate (o3B) | − |
| pNP-phosphoryl-choline (CCH) | + |

Color code for colonies of coryne-shaped organisms: Type No. 60 according to Seiler (1983)

For the process for the production of hydroxylated pyrazines or quinoxalines,
a pyrazine of general formula I as substrate:

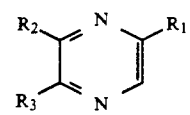

I or a quinoxaline of general formula II as substrate:

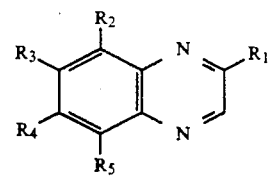

II wherein $R_1$ is a $C_1$-$C_4$ alkyl group or a halogen atom and $R_2$, $R_3$, $R_4$ and $R_5$ are the same or different and each is a hydrogen atom, a $C_1$-$C_4$ alkyl group or a halogen atom is converted with the microorganisms set out above to a hydroxylated pyrazine of general formula III

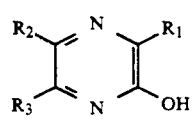

III or to a hydroxylated quinoxaline of general formula IV:

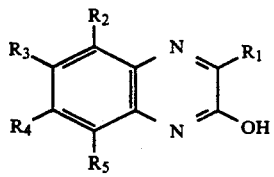

wherein $R_1$, $R_2$, $R_3$, $R_4$ and $R_5$ have the above-stated meaning, and the concentrated product is isolated.

Compounds of general formula I or II are suitable as pyrazines or quinoxalines to be hydroxylated.

Preferably, pyrazine derivatives or quinoxaline derivatives of general formula I or II are hydroxylated by these microorganisms wherein $R_1$ is a methyl group, ethyl group or a chlorine atom and $R_2$ and $R_3$ are the same or different and each is a hydrogen atom, a methyl group or a chlorine atom.

Usually, the microorganisms are cultivated before the actual process (substrate reaction) in a medium containing a growth substrate. Growth substrate 2,5-dimethylpyrazine is suitably used in an amount of 0.001 to 10 percent (w/v), relative to the culture medium, preferably in an amount of 0.001 to 5 percent (w/v), relative to the culture medium.

The enzymes of the microorganism responsible for hydroxylation are suitably induced by 2,5-dimethylpyrazine. The compound used for induction can either be present during the reaction of the heterocyclic substrate or the feed of the induction compound is stopped during the reaction. Preferably, the feed of the compound used for induction is stopped during the reaction of the heterocyclic substrate either by stopping the feed or by, for example, centrifuging the cells.

Before adding the substrate, the cells are suitably drawn in up to an optical density of 100 at 650 nm, preferably up to an optical density of 10 to 60 at 650 nm.

As the substrate for the microorganisms, both for the cultivation and for the actual process, which are those normally used among those skilled in the art, the medium, whose composition is indicated in Table 1 below, is preferably used.

The actual process (substrate reaction) then takes place usually with resting cells.

The pyrazine or quinoxaline of general formula I or II can be fed once or continuously to the cell suspension, preferably so that the substrate concentration in the culture medium does not exceed 20 percent (w/v). In particular, the substrate concentration does not exceed 5 percent (w/v) in the culture medium.

The reaction is performed in a pH range of 4 to 10, preferably 6 to 8. Usually, the reaction is performed at a temperature of 0° to 50° C., preferably at 20° to 40° C.

After the reaction, the hydroxylated heterocycles can be isolated in a known way, e.g., by extraction with chlorinated hydrocarbons.

EXAMPLE 1

Isolation of 2 5-dimethylpyrazine-metabolizing microorganisms

Aerobic 2,5-dimethylpyrazine-metabolizing microorganisms were concentrated in the A+N medium (Table 1) with adding 0.1 percent (w/v) of 2,5-dimethylpyrazine as sole carbon, nitrogen and energy source. The general techniques for isolating microorganisms are described, for example, in G. Drews, Mikrobiologisches Praktikum [Microbiological Workshop], 4th Ed., Springer Verlag, (1983). As an inoculum, samples from the earth, sewage treatment plants, compost and anthills were used. The concentrations were drawn into shaking flasks at 30° C.. After over-inoculating three times in fresh medium, the concentrations of the same medium were streaked by adding 16 g of agar per liter and incubated at 30° C. After repeated streaking on agar medium, pure cultures were able to be isolated.

TABLE 1

| A + N medium | |
|---|---|
| Composition | Concentration (mg/l) |
| $(NH_4)_2SO_4$ | 2000 |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| pyridoxal hydrochloride | $10 \cdot 10^{-3}$ |
| riboflavin | $5 \cdot 10^{-3}$ |
| nicotinic acid amide | $5 \cdot 10^{-3}$ |
| thiamine hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $10 \cdot 10^{-3}$ |
| $NiCl_2.6H_2O$ | $20 \cdot 10^{-3}$ |
| $Na_2MoO_4.2H_2O$ | $30 \cdot 10^{-3}$ |
| $EDTANa_2.2H_2O$ | $5 \cdot 10^{-3}$ |
| $FeSO_4.7H_2O$ | $2 \cdot 10^{-3}$ |
| (pH of the solution was adjusted to 7.0) | |

EXAMPLE 2

Reaction of 2,5-dimethylpyrazine to 2,5-dimethyl-3-hydroxypyrazine

Rhodococcus erythropolis (DSM No. 6138) was drawn in the A+N medium with 0.1 percent (w/v) of 2,5-dimethylpyrazine in a fermenter at pH 7 and a temperature of 25° C. Then, the cells were centrifuged and resuspended in the A+N medium and adjusted to an optical density of 10 at 650 nm. This cell suspension was added in a shaking flask and mixed with 92 mmol of 2,5-dimethylpyrazine per liter. After an incubation of 4 hours at 25° in a shaking machine, 83 mmol of 2,5-dimethyl-3-hydroxypyrazine per liter, corresponding to a yield of 90 percent, was detected.

EXAMPLES 3 TO 9

Examples 3 to 9 were performed according to Example 2 and are summarized in Table 2.

TABLE 2

| Example | Substrate | Concentration of the heterocycle in % (w/v) in the medium | Reaction time in hours | End Product | Yield in % |
|---|---|---|---|---|---|
| 3 | 2-methylpyrazine | 0.2 | 1 | 3-hydroxy-2-methylpyrazine | 90 |
| 4 | 2-chloropyrazine | 0.2 | 24 | 3-hydroxy-2-chloropyrazine | 60 |
| 5 | 2-ethylpyrazine | 0.2 | 24 | 3-hydroxy-2-ethylpyrazine | 80 |
| 6 | 2,6-dimethylpyrazine | 0.2 | 1 | 3-hydroxy-2,6-dimethylpyrazine | 90 |
| 7 | 2,5,6-trimethyl-pyrazine | 0.2 | 6 | 3-hydroxy-2,5,6-trimethylpyrazine | 90 |
| 8 | 6-chloro-2,5-dimethylpyrazine | 0.2 | 1 | 3-hydroxy-6-chloro-2,5-dimethylpyrazine | 90 |
| 9 | 2-methyl-quinoxaline | 0.4 | 5 | 3-hydroxy-2-methylquinoxaline | 50 |

What is claimed is:

1. Microorganisms, substantially in pure form, selected from the group consisting of (a) *Rhodococcus erythropolis* DSM 6138, (b) Arthrobacter sp. DSM 6137, (c) a descendant of microorganism (a), and (d) a descendant of microorganism (b), descendant (c) and descendant (d) each being capable of growing with 2,5-dimethylpyrazine as sole carbon, nitrogen and energy source, and being capable of converting a pyrazine of formula I as substrate:

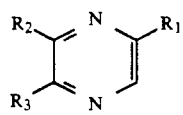

I or a quinoxaline of general formula II as substrate:

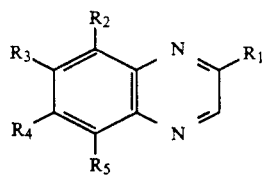

II wherein $R_1$ is a $C_1$-$C_4$ alkyl group or a halogen atom and $R_2$, $R_3$, $R_4$ and $R_5$ are the same or different and each is a hydrogen atom, a $C_1$-$C_4$ alkyl group or a halogen atom, to a hydroxylated pyrazine of general formula III:

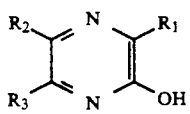

III or to a hydroxylated quinoxaline of general formula IV:

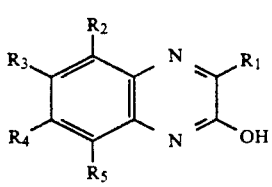

IV wherein $R_1$, $R_2$, $R_3$, $R_4$ and $R_5$ have the above-stated meaning, respectively and the hydroxylated pyrazine of formula III or hydroxylated quinoxaline of formula IV being accumulated in the growth medium.

2. *Rhodococcus erythropolis* DSM 6138, substantially in pure form.

3. Arthrobacter sp. DSM 6137, substantially in pure form.

4. Biologically pure culture of the microorganism selected from the group consisting of (a) *Rhodococcus erythropolis* DSM 6138, (b) Arthrobacter sp. DSM 6137, (c) a descendant of microorganism (a), and (d) a descendant of microorganism (b), descendant (c) and descendant (d) each being capable of growing with 2,5-dimethylpyrazine as sole carbon, nitrogen and energy source, and being capable of converting a pyrazine of the formula I as substrate:

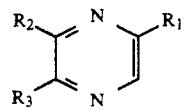

I or a quinoxaline of general formula II as substrate:

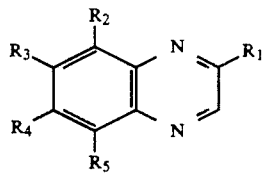

II wherein $R_1$ is a $C_1$-$C_4$ alkyl group or a halogen atom and $R_2$, $R_3$, $R_4$ and $R_5$ are the same or different and each is a hydrogen atom, a $C_1$-$C_4$ alkyl group or a halogen atom, to a hydroxylated pyrazine of general formula III:

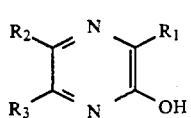

III or to a hydroxylated quinoxaline of general formula IV:

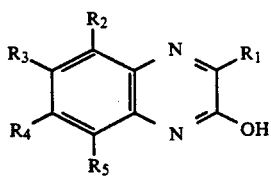

wherein $R_1$, $R_2$, $R_3$, $R_4$ and $R_5$ have the above-stated meaning, respectively and the hydroxylated pyrazine of formula III or hydroxylated quinoxaline of formula IV being accumulated in the growth medium.

5. The microorganism of claim 4 wherein hydroxylation enzymes of the microorganism have been induced with 2,5-dimethylpyrazine.

6. Biologically pure culture of *Rhodococcus erythropolis* DSM 6138.

7. Biologically pure culture of Arthrobacter sp. DSM 6137.

* * * * *